United States Patent
Liang (10) Patent No.: US 10,048,516 B2
(45) Date of Patent: Aug. 14, 2018

(54) METHODS AND SYSTEMS FOR MEASURING HUMAN FACES AND EYEGLASS FRAMES

(71) Applicant: PERFECT VISION TECHNOLOGY (HK) LTD., Tsuen Wan (HK)

(72) Inventor: Junzhong Liang, Fremont, CA (US)

(73) Assignee: PERFECT VISION TECHNOLOGY (HK) LTD., Tsuen Wan, NT (HK)

( * ) Notice: Subject to any disclaimer, the term of this patent is extended or adjusted under 35 U.S.C. 154(b) by 0 days.

(21) Appl. No.: 15/372,676

(22) Filed: Dec. 8, 2016

(65) Prior Publication Data

US 2018/0164609 A1    Jun. 14, 2018

(51) Int. Cl.
| | |
|---|---|
| *A61B 3/10* | (2006.01) |
| *G02C 13/00* | (2006.01) |
| *A61B 3/11* | (2006.01) |
| *A61B 3/00* | (2006.01) |

(52) U.S. Cl.
CPC .......... *G02C 13/005* (2013.01); *A61B 3/0025* (2013.01); *A61B 3/10* (2013.01); *A61B 3/111* (2013.01); *G02C 13/00* (2013.01); *G02C 13/003* (2013.01)

(58) Field of Classification Search
CPC .... G02C 13/005; G02C 13/003; G02C 13/00; G02C 7/027; G02C 7/024; A61B 3/111; A61B 3/11; A61B 3/0025; A61B 3/10
USPC .................................................. 351/204, 200
See application file for complete search history.

(56) References Cited

U.S. PATENT DOCUMENTS

| | | | |
|---|---|---|---|
| 6,095,650 A * | 8/2000 | Gao | G02C 13/005 351/227 |
| 7,221,437 B1 | 5/2007 | Schaefer | |
| 9,395,562 B1 | 7/2016 | Nguyen et al. | |
| 9,628,697 B2 * | 4/2017 | Choukroun | A61B 3/111 |
| 2001/0026351 A1 | 10/2001 | Gao et al. | |
| 2004/0189935 A1* | 9/2004 | Warden | G02C 7/027 351/204 |
| 2008/0084481 A1 | 4/2008 | Lindsay | |
| 2009/0051871 A1* | 2/2009 | Warden | G02C 13/003 351/204 |
| 2010/0283844 A1* | 11/2010 | Sayag | G02C 13/003 348/78 |
| 2011/0063449 A1 | 3/2011 | Lee | |

(Continued)

OTHER PUBLICATIONS

International Search Report and Written Opinion dated Jul. 27, 2017 for PCT Patent Application No. PCT/US2016/065576.

(Continued)

*Primary Examiner* — William R Alexander
(74) *Attorney, Agent, or Firm* — The Mueller Law Office, P.C.

(57) ABSTRACT

Methods and systems for making measurements for eyeglass frames worn by human subjects include capturing, using a first digital camera module, a plurality of images of a head of a tested subject wearing an eyeglass frame. The plurality of images comprises a front view image and a side view image of a face of the tested subject. A second camera module is used to monitor a top view of the head. A computer module is used to process the front view image and the side view image. The front view image is used to determine a pupillary distance and a segment height, and the side view image is used to determine a vertex distance and a pantoscopic tilt.

14 Claims, 7 Drawing Sheets

(56) References Cited

U.S. PATENT DOCUMENTS

| | | | |
|---|---|---|---|
| 2011/0242481 A1* | 10/2011 | Wada | G02C 13/005 351/204 |
| 2012/0008090 A1* | 1/2012 | Atheimer | G02C 7/025 351/159.75 |
| 2013/0222684 A1* | 8/2013 | Mueller | F16M 11/18 348/373 |
| 2013/0222764 A1* | 8/2013 | Thompson | A61B 3/103 351/209 |
| 2015/0015848 A1* | 1/2015 | Haddadi | A61B 3/113 351/221 |
| 2016/0166145 A1* | 6/2016 | Choukroun | A61B 3/111 351/246 |
| 2016/0202499 A1 | 7/2016 | Farache | |
| 2016/0327811 A1* | 11/2016 | Haddadi | G02C 13/003 |
| 2016/0357032 A1* | 12/2016 | Cabeza-Guillen | G02C 13/005 |
| 2017/0038608 A1* | 2/2017 | Cabeza-Guillen | G02C 13/005 |

OTHER PUBLICATIONS

International Search Report and Written Opinion dated Jul. 27, 2017 for PCT Patent Application No. PCT/US2016/065590.
Office Action dated Jan. 12, 2018 for U.S. Appl. No. 15/372,684.

* cited by examiner

METHODS AND SYSTEMS FOR MEASURING HUMAN FACES AND EYEGLASS FRAMES

RELATED APPLICATIONS

This application is related to Liang, U.S. patent application Ser. No. 15/372,684, entitled "Methods and Systems for Measuring Human Faces for Fitting, Selecting and Optimizing Eyeglasses" and filed on Dec. 8, 2016, which is hereby incorporated by reference for all purposes.

BACKGROUND

A good pair of eyeglasses for vision correction of human eyes requires seeing well through the lenses. Seeing well through the lenses requires obtaining the best refractive prescription possible, and mounting the lenses into eyeglass frames at the perfect location. Mounting the lenses into eyeglass frames involves measuring pupil distances of left and right eyes with a device such as the Essilor® PD meter, and measuring parameters related to the eyeglass frames for personalized free-form lenses. The parameters include, for example, segment height, vertex distances, and pantoscopic tilts, which are measured using systems like Accufit® Digital Measurement systems from LensCrafters™ or i.Terminal 2® from Zeiss. Fitting of the frames also may include virtually trying-on eyeglass frames using tablet-based software applications that capture videos of patients from different perspective views and allow customers to select styles of eyeglass frames.

The Essilor PD meter provides precise measurements of pupil distances, but cannot get the other measurements like Accufit Digital Measurement systems, iTerminal 2, or tablet-based apps for a virtual try-on of eyeglass frames.

Systems like Accufit Digital Measurement and i.Terminal 2 can provide measurements related to the eyeglass frames for personalized free-form lenses, but these systems have issues in matching the pupil distances measured with Essilor PD meters and cannot provide a virtual try-on like the tablet-based apps.

Tablet-based apps are inexpensive tools for providing virtual try-on capabilities, but cannot provide the same precision and reliability in measuring pupilary distance like Essilor PD meter, and the other parameters relating the eyeglass frames for personalized free-form lenses like Accufit Digital Measurement and i.Terminal 2.

Consequently, although many configurations and methods for vision correction are known in the art, all of them suffer from one or more disadvantages. Thus, there is a need to provide improved methods and systems for measuring human faces for fitting of eyeglass frames.

SUMMARY

In some embodiments, a method for making measurements for eyeglass frames worn by human subjects includes capturing, using a first digital camera module, a plurality of images of a head of a tested subject wearing an eyeglass frame. The plurality of images includes a front view image and a side view image of the head of the tested subject. A second camera module is used to monitor a top view of the head. A computer module is used to process the front view image and the side view image. The front view image is used to determine a pupillary distance and a segment height, and the side view image is used to determine a vertex distance and a pantoscopic tilt.

A system for making measurements for eyeglass frames worn by human subjects includes a first digital camera module, a second camera module and a computer module. The first digital camera module is positioned to capture a plurality of images of a head of a tested subject wearing an eyeglass frame. The plurality of images includes a front view image and a side view image of the head. The second camera module is positioned to monitor a top view of the head. The computer module processes the front view image, the side view image and the top view. The front view is used to determine a pupillary distance and a segment height the side view image is used to determine a vertex distance and a pantoscopic tilt, and the top view is used to determine an orientation of the eyeglass frame with respect to an optical axis of the first digital camera module.

In other embodiments, a method for making measurements for eyeglass frames worn by human subjects includes capturing, using a digital camera module, a plurality of images a head of a tested subject wearing an eyeglass frame. The plurality of images includes a front view image and a side view image of the head. A sensor module is used to determine a depth from the digital camera module to the tested subject. The sensor module can be i) a second camera that captures the side view, ii) a 3D camera that captures two of the front view images of the tested subject, or iii) a module comprising an active source and a distance sensor. The determined depth from the camera module to the tested subject is used for converting pixel coordinates of the digital camera module to physical measurements at a plane of the eyeglass frame. A computer module is used for processing the front view image to determine a pupillary distance and a segment height, and for processing the side view image to determine a vertex distance and a pantoscopic tilt.

DETAILED DESCRIPTION

As described in the background, there are a number of systems for measuring the human face and eyeglass frames. Parameters for fitting eyelgasses include pupillary distance, segment height, vertex distance, and pantoscopic tilt. Pupillary distance (PD) is the distance from the center of the face to each of the left and right pupils (left PD and right PD). Segment height—also referred to as seg height or SH—is the vertical distance from the bottom of the eyeglass lens to the pupil center of the eye. Vertex distance is the distance between the back surface of the eyeglass lens and the front surface of the cornea. Pantoscopic tilt is the angle that the lower rim of the eyeglass frame is tilted toward the wearer's face.

Figure 1:
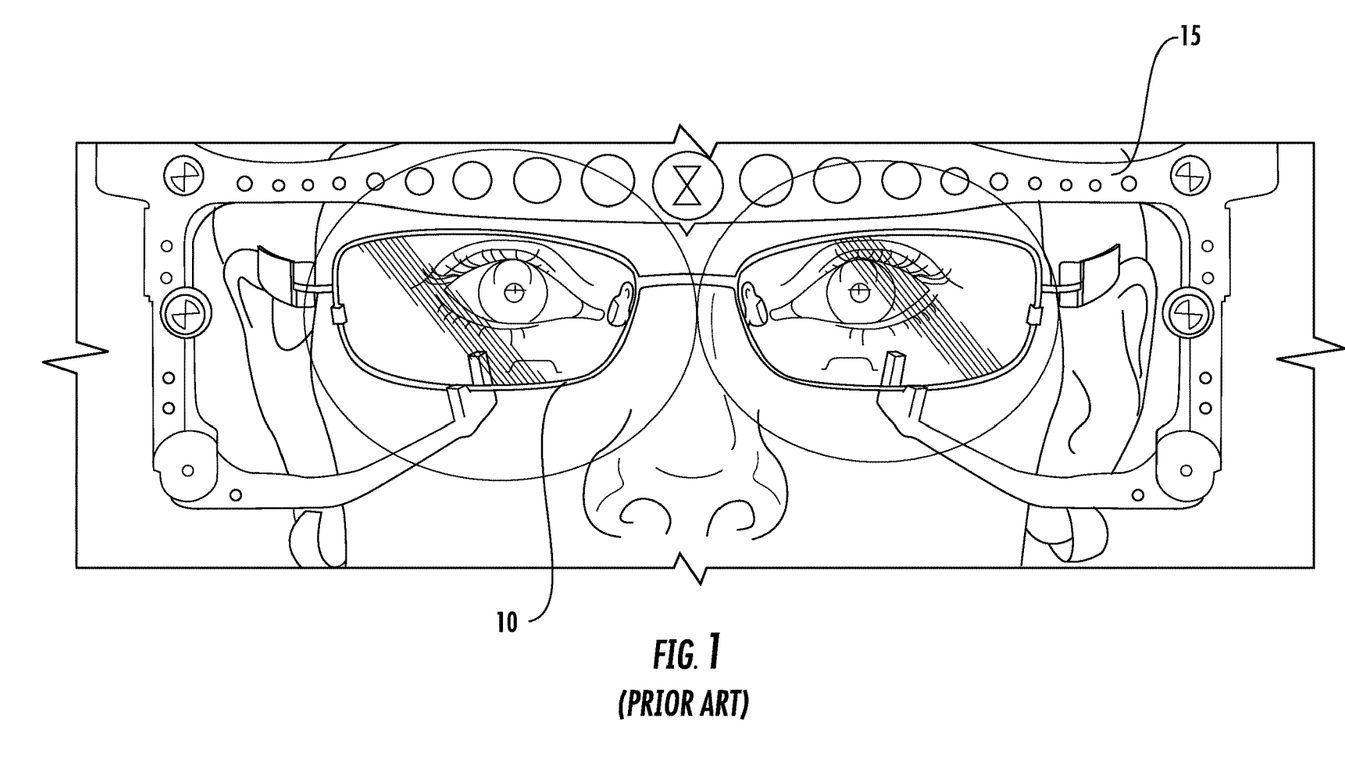
FIG. 1 shows a typical front-view image of a tested subject wearing an eyeglass frame with a frame attachment as known in the prior art.

FIG. 1 shows a typical front view image of a tested subject wearing an eyeglass frame 10 with a frame attachment 15 mounted to the eyeglass frame, for the measurement of a human face with eyeglasses in the prior art. This kind of frame attachment is universal and necessary for conventional image-based systems that measure pupillary distances, segment height and vertex distances, because the image dimension captured by the camera must be scaled from a number of pixels to milimeters.

Getting rid of the frame attachments for fitting eyeglasses is desirable for a number reasons. First, adding the frame attachment not only alters the appearance of the eyeglass frames, but also adds significant weight to the eyeglass frame during a measurement and even can change the balance of the eyeglass frame on the human face. Second, mounting the frame attachment to the frame can be difficult for many frame styles. Third, errors in mounting the frame attachment to the frame can cause measurement errors.

Figure 2:
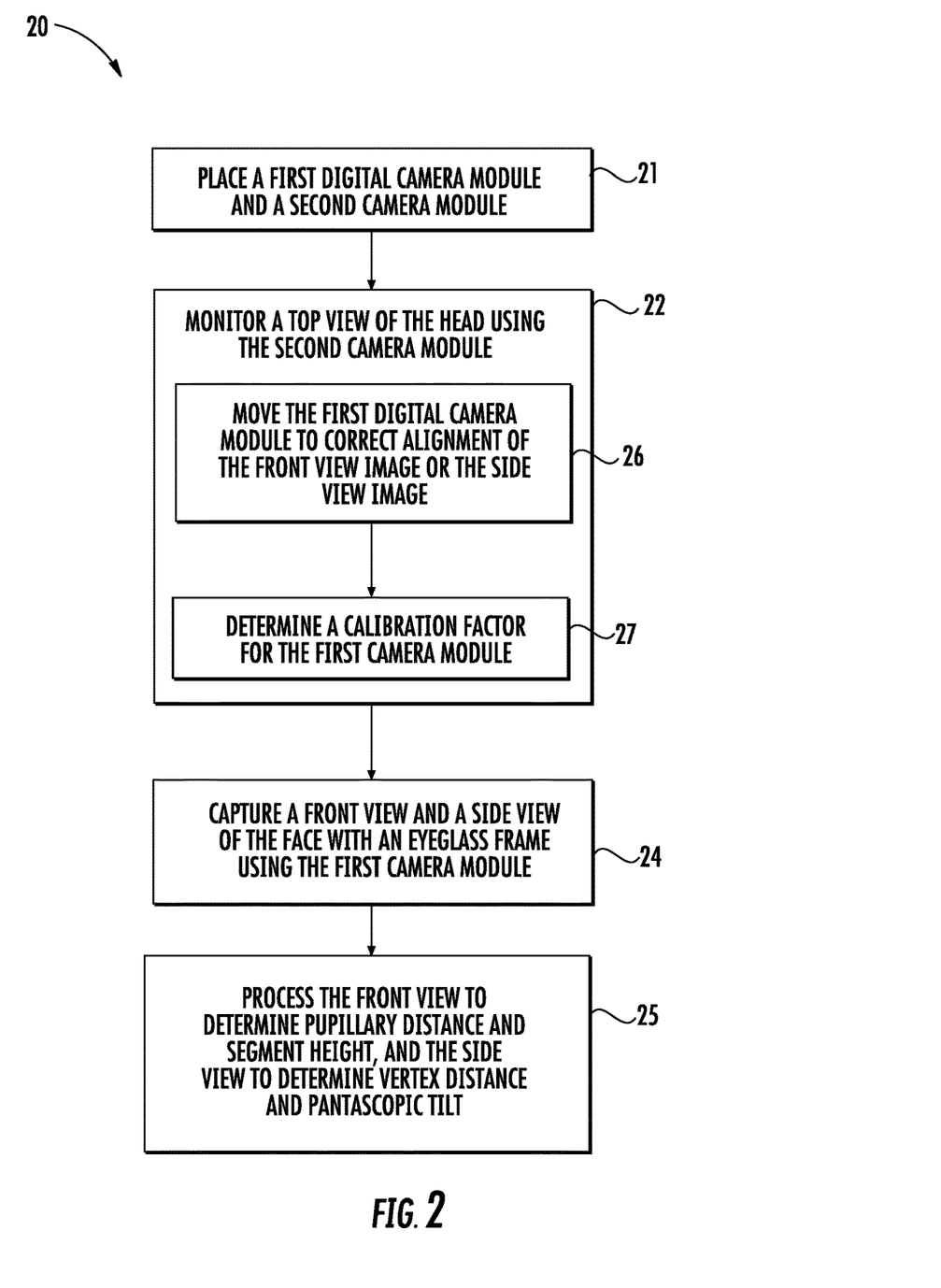
FIG. 2 shows a flow chart of a method for measuring human faces and eyeglass frames according to embodiments of the present disclosure.

FIG. 2 shows a flow chart of an improved image-based method for measuring human faces and eyeglass frames according to embodiments of the present disclosure. Features of the method include eliminating the frame attachment and providing more reliable measurement for the pupillary distances, seg heights, and vertex distances. While it is known in the art to use a digital camera module for capturing a front view or a side-view image of a tested subject, the present methods also include placing a second camera module to capture a top view of a tested subject. In the present methods, a first, front-view camera module and a second, top-view camera module are mounted on two axes of a single mechanical structure. The top-view camera provides reliable distance and orientation estimates of the test object such as an eyeglass frame or the face of the human subject wearing the eyeglass frame. From the reliable estimate for the distance from the test object to the front-view camera module, one can determine the conversion factors from image pixels to millimeters (or other distance dimension such as inches or centimeters) for the images of the first, front-view camera module. The top view camera also provides an assessment of the alignment of the front view camera, such that the alignment can be corrected if needed.

Flow chart 20 of FIG. 2 shows a method for making measurements for human faces with eyeglass frames in accordance with embodiments of the present disclosure. In step 21, a first digital camera module and a second camera module are placed for capturing desired views of the head of a tested subject (e.g., patient) wearing an eyeglass frame. The eyeglass frame is a desired frame that is being fitted to the patient's face, and no frame attachment is needed to be mounted to the eyeglass frame during the fitting. The first digital camera module is used to capture a plurality of images, including at least a front view image and a side view image of the face of the tested subject. The first digital camera module may also be referred to as a first camera module or a front view camera in this disclosure. The second camera module, which may be digital, is used for monitoring a top view of a tested subject as shown in step 22. For example, the second camera module may be positioned above the head of the tested subject. Monitoring the top view of the head is used to determine an orientation of the eyeglass frame with respect to an optical axis of the first digital camera module.

In step 24, images of the front view of the face and the side view of the face with an eyeglass frame are captured using the first camera module. In step 25, a computer module processes the front view and the side view images, where the front view is used to determine pupillary distances of the eye and seg height, and the side view of the face with an eyeglass frame is used to determine vertex distance and pantoscopic tilts. The computer module is connected to the first and the second camera modules for processing, and optionally storing, the images.

Steps 26 and 27 describe details of how the top view is utilized. If the first camera module is not aligned properly with respect to the eyeglass frame or the face of the tested subject, step 26 involves moving, using a motion control module, the first digital camera module to correct alignment of the front view image and/or the side view image. The first digital camera module is coupled to the motion control module, and correction of alignment of the first camera module is achieved by changing a perspective angle of the first camera module. Movement of the first digital camera by the motion control module is controlled by the computer module to align the orientation of the front view image or the side view image with an optical axis of the first digital camera module, based on the top view of the head monitored by the second camera module. The correction of alignment is based on determining an angle error between the eyeglass frame and optical axis of the first camera module, using the top view from the second camera module to provide guidance on the misalignment. The optical axis (i.e., center line) is fixed for both the front and top view cameras, and the camera alignment process assumes that the eyeglass frame is sitting properly on the patient's face. The angle of the eyeglass frame relative to the fixed axis is the angular error or offset. The angular offset in the top view image is determined by either manually locating the eyeglass frame or by using automated image processing.

In some embodiments, the motion control module moves the first digital camera module with respect to the head to correct alignment without any assistance of the tested subject. The corrected angle results in the first camera module being able to capture a perfect front view and a perfect side view, where the motion control module is used to move the first digital camera module such that an optical axis of the first digital camera module is perpendicular to a plane of the eyeglass frame. In one embodiment, the first and the second camera are mounted on a mechanical structure of a motion control module for moving the camera modules around the head of the tested subject. This mounting of the cameras on a movable structure allows the necessary corrections to be made if the front view or the side view of the face are not perfectly aligned. In some embodiments, the motion control module has a rotation arm to which the first camera module is coupled, and the moving comprises rotating the first digital camera module around the head of the tested subject. In some embodiments, the second camera module is mounted on the rotation arm, where orientations of image coordinates for the second camera module rotate together with the rotation arm. In one embodiment, the motion control module also includes a translation module for 3D X-Y-Z movements in order to accommodate for various initial positions of the head of the tested subject.

In step 27, a calibration factor for the first digital camera module is determined, using the top view of the head from the second camera module. Since images from the digital cameras have units in pixels and the objects for the image are away from the camera at a distance, conversion of the dimensions of the object, such as pupillary distance, from pixels to millimeters is necessary. The calibration factor is based on step 26 in which the top view of the head from the second camera module is used to determine an orientation of the eyeglass frame relative to an optical axis of the first digital camera module. The calibration factor of step 27 is determined by using the top view of the head from the second camera module to determine a distance from the first digital camera module to the eyeglass frame or to a facial feature of the tested subject. The determined distance, such as the distance between the first digital camera module and the eyeglass frame, is used to determine the calibration factor.

The calibration process first involves placing a target with a precision ruler at a calibration distance $D_0$ in mm, taking a picture of the target using the first camera module, and determining a baseline calibration factor $C_0$ in mm/pixel between the image space in pixels and object space in mm if the object is at the distance of $D_0$. For another object at a known distance $D_1$, the calibration factor will be $C_0*(D_1/D_0)$. Therefore, knowing the distance of the frame to the camera is essential for calculating dimensions (e.g., pupillary distance) without a frame attachment, compared to use of a frame attachment as in the prior art.

Once images of the first and second camera module are captured, features on eyeglass frames as well as features of human face such as pupil and corneal vertex can be manually determined by an operator or automatically determined though image processing.

Figure 3A:
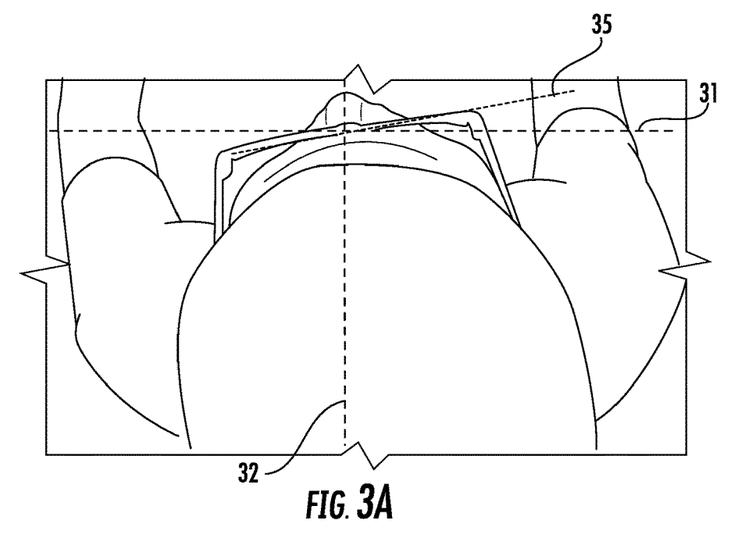
FIG. 3A shows an example top view of a tested subject when the face/frame and the image plane of the front view camera has an angular offset.
Figure 3B:
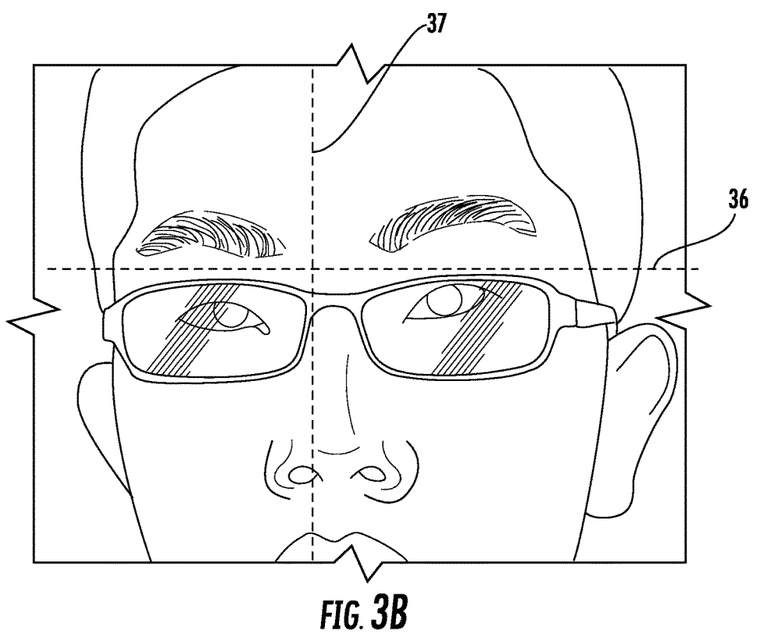
FIG. 3B shows an example front view of the subject of FIG. 3A with the eyeglass frame.

FIGS. 3A-3B and 4A-4B show example views from the first and second camera modules. As shown in FIG. 3A, a typical top view of a tested subject with an eyeglass frame is monitored, where the monitoring may involve real-time viewing, and/or capturing and storing the image in some embodiments. As designated by the dashed lines that represent the horizontal (x) axis 31 and vertical (z) axis 32 of the top-view camera, the plane 35 of the eyeglass frame in FIG. 3A is not aligned to the horizontal axis 31 of the top-view camera. This indicates that the plane 35 of the eyeglass frame has an angular offset with respect to the image plane of the first camera module. This offset is also validated by the image in FIG. 3B, showing an asymmetrical front view of the tested subject captured by the first camera module. The first, front view camera has a horizontal (x) axis 36 and a vertical (y) axis 37, where the eyeglass frame is offset from both axes 36 and 37.

Figure 4A:
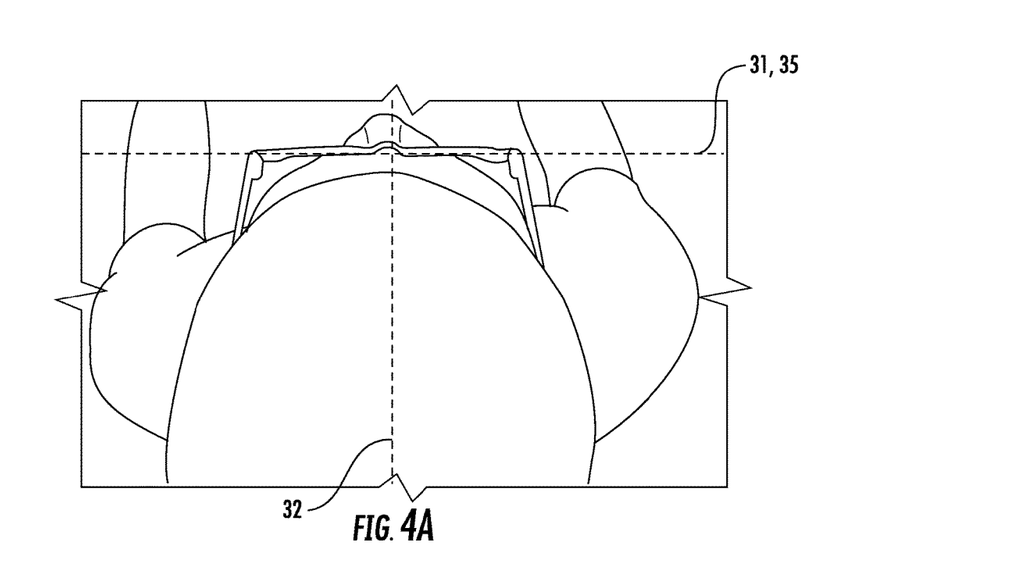
FIG. 4A shows an example top view of a tested subject when the face/frame and the image plane of the front view camera has no angular offset.
Figure 4B:
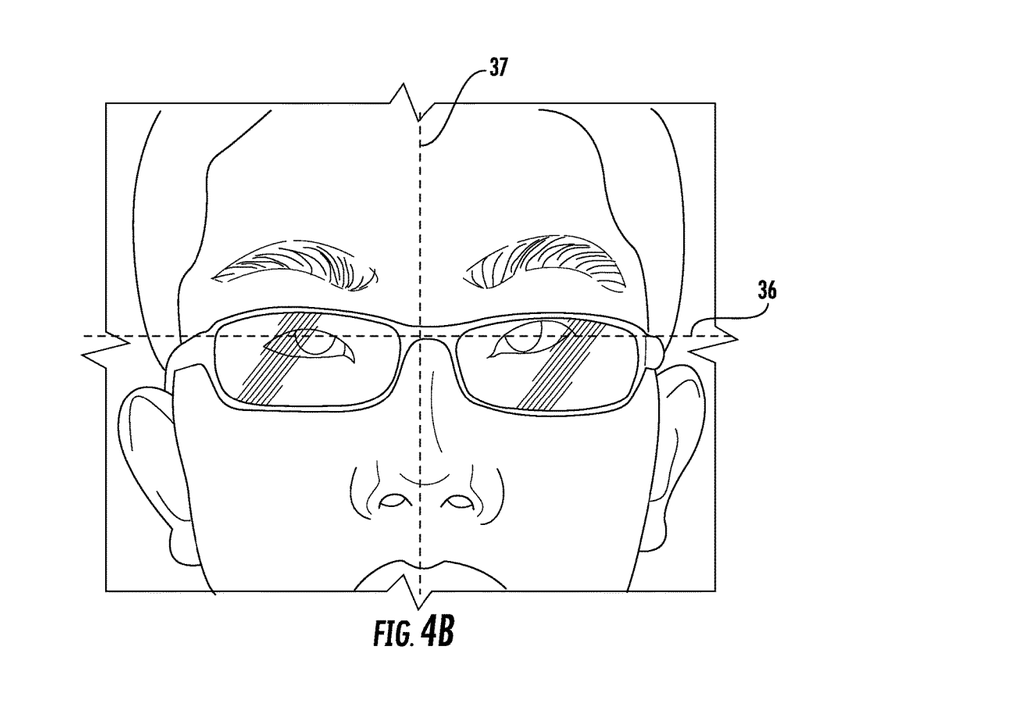
FIG. 4B shows an example front view of the subject of FIG. 4A with the eyeglass frame.

Using the angular offset detected by the top-view camera in FIG. 3A, the first camera module can be moved, such as being rotated around the head, for correcting the orientation error of the front and/or side views, as described in step 26 of FIG. 2. FIG. 4A shows a top view of a tested subject when the angular error between eyeglass frame and image plane of the front-view camera is corrected, indicating that the plane of the eyeglass frame is now parallel to the horizontal axis 31 of the top view camera. This alignment is also validated in the image of FIG. 4B, showing the symmetrical front view of the tested subject captured by the first, front view camera module. That is, the vertical axis 37 is aligned with the centerline of the tested subject's face, and the horizontal axis 36 is aligned with the pupils of the tested subject.

Figure 5:
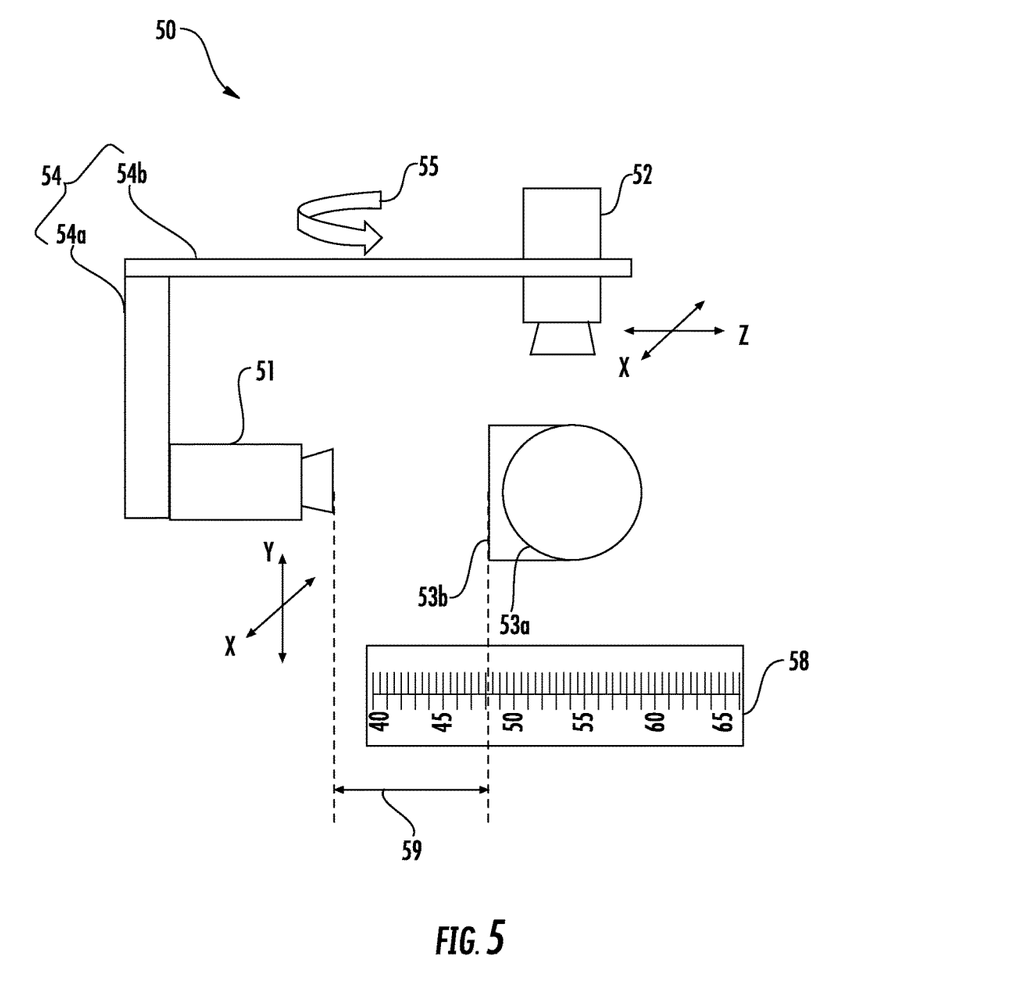
FIG. 5 illustrates an example system for measuring human faces and eyeglass frames, in accordance with some embodiments.

FIG. 5 is a simplified illustration of a side view of a system 50 for measuring human faces and eyeglass frames. FIG. 5 shows the relation of a first digital camera module 51 (front view of the tested subject) and a second camera module 52 (top view of the tested subject), and their interaction in providing accurate eyeglass fitting for the patient's head 53a. Mechanical structure 54 comprises a mounting arm 54a to which the first (front view) camera module 51 is mounted for capturing front and side views, and a rotation arm 54b to which second (top view) camera module 52 is mounted for capturing top views. The mounting arm 54a and rotation arm 54b are part of the single mechanical structure 54. The mounting arm 54a has a first axis (vertical y-axis in FIG. 5) and the rotation arm 54b has a second axis (horizontal z-axis in FIG. 5), where the second axis is orthogonal to the first axis. Movement of the mounting arm 54a and rotation arm 54b are part of a motion control module, where additional components (not shown) of the motion control module are connected to a computer module for controlling movement of the mechanical structure 54 and positioning of first and second camera modules 51 and 52.

An eyeglass frame is worn by the tested subject. The plane of the eyeglass frame 53b—that is, the plane of the rims that hold the lenses—is made parallel to the image plane of the first camera module 51, as monitored by the top view camera 52 and controlled by rotating the rotation arm 54b (rotation around the y-axis, as indicated by arrow 55) if the eyeglass frame in the top-view camera 52 is not parallel to the x-axis of the top view camera 52. Once the first camera module 51 has been aligned with respect to the eyeglass frames (and consequently the patient's face assuming that the frames are being worn properly), the distance from the eyeglass frame 53b to the first camera module 51 can then be determined. If the front view camera 51 captures an object in x-horizontal and y-vertical directions, the top view camera 52 will capture the same object in x-horizontal and z-depth direction in reference to the first camera module. During a calibration process without the tested subject in the system, a ruler 58 is placed along the z-axis of the top view camera 52. In the example of FIG. 5, a top-view image of the ruler 58 is shown with known distances from the first camera starting from 40 mm. Once the top view image of the head 53a and the eyeglass frame 53b is acquired, the distance from the eyeglass frame 53b to the first camera module 51 can be determined based on the relationship of the eyeglass frame 53b to the image of the ruler 58, as indicated by depth distance 59.

Knowing the distance from the eyeglass frame 53b to the front view camera 51, the conversion factor from image pixels to a physical measurement (e.g., millimeters) can be determined for the front view camera, which can then be used to convert pupillary distances and seg heights from the front view image, and vertex distances from the side view image, in pixels to millimeters. As a result, the need for a conventional frame attachment is able to be completely eliminated, which has tremendous advantages over the technology in the prior art.

Figure 6:
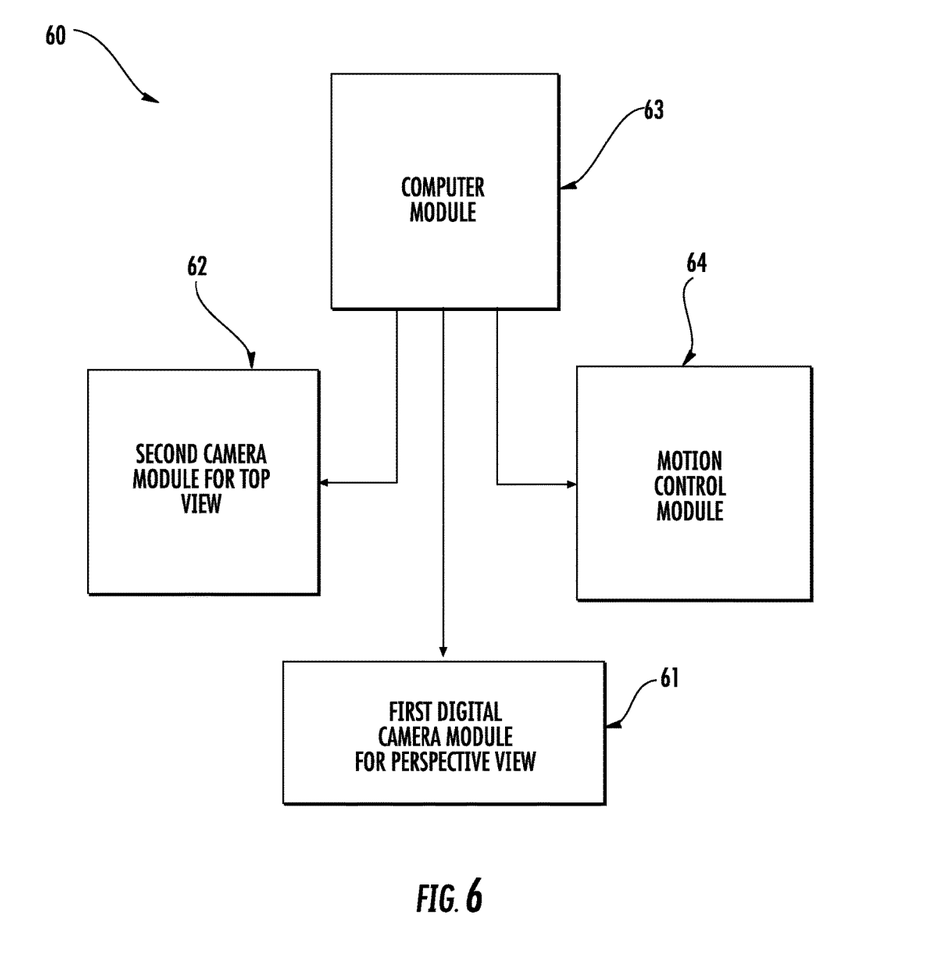
FIG. 6 shows a block diagram of the system of FIG. 5.

FIG. 6, shows a block diagram of an example system 60 for measuring human faces and eyeglass frames according to the present disclosure. The system 60 includes a first digital camera module 61 that captures a plurality of digital images of a head of a tested subject wearing an eyeglass frame. The digital images include those for a front view and a side view of the face, which together can be categorized as perspective views. The first digital camera module 61 includes a lens, an image sensor, and control electronics. The system 60 also includes a second camera module 62 positioned to capture a top view of the head, such as above the head of the tested subject. The first digital camera 61 is positioned to capture the front view and side view of a tested subject, and the second camera module 62 is positioned to capture the top view of the same tested subject. The camera modules 61 and 62 are mounted on two axes of a single mechanical structure of motion control module 64, so that 3D (x, y, z) coordinates of any feature observed by both of these cameras can be determined.

A computer module 63 is connected to the first digital camera module 61 for processing the front view image to determine pupillary distance and seg height, and for processing the side view image to determine vertex distance and pantoscopic tilt. The computer module 63 can also be used for storing the various images from the first and second camera modules 61 and 62. The computer module 63 is also connected to the second camera module to monitor images viewed by the second, top view camera module for 1) determining the orientation of the eyeglass frame relative to an optical axis of the first digital camera module, and 2) determining the distance from the first digital camera module to the eyeglass frame or a facial feature of the tested subject. The determined distance information is used for determining a calibration factor, such as in mm/pixel, for the images of the first digital camera module. The determined orientation data from the second camera module is used for controlling the perspective view angle of the first camera module, such as for moving the first camera module to correct its alignment with the face of the tested subject.

In one embodiment, the first camera module 61 and optionally the second camera module 62 can be rotated around an axis in the system with a motion control module 64. The motion control module 64 can move the first camera module around the head which makes the necessary corrections if the front view or the side view of the face are not perfectly aligned. The corrections can be made without any assistance of the test subject in response to request of an operator. The face misalignment is monitored by the top view of the head from the second camera module. In some embodiments, the motion control module 64 includes a controlled rotation arm to which the first digital camera module is coupled. In such embodiments, the computer module controls the motion control module to move the rotation arm such that an optical axis of the first digital camera module is perpendicular to a plane of the eyeglass frame, where the control of the motion control module uses the top view from the second camera module. For example, the optical axis 32 in FIG. 4A is made perpendicular to the plane 35 of the eyeglass frame. In some embodiments both the first and second camera modules are mounted on the rotation arm, and an image coordinate axis (the x-axis) for the second camera module rotates together with the rotation arm as shown in FIG. 5.

In one embodiment, the mechanical structure for mounting the first and second camera module is further configured to be moved linearly such as in 3D X-Y-Z directions to accommodate different initial positions of the head and eyeglass frame of the tested subject. For example, the mechanical structure 54 of FIG. 5 can be configured with a translation module to move the first camera module 51 and optionally the second camera module 52 in the X, Y and Z directions. The translational movements of the first and second camera modules 51 and 52 can be performed independently of each other. These additional degrees of freedom in moving the camera modules can assist in accommodating variations in head position among test subjects, such as due to differences in height and posture.

Figure 7:
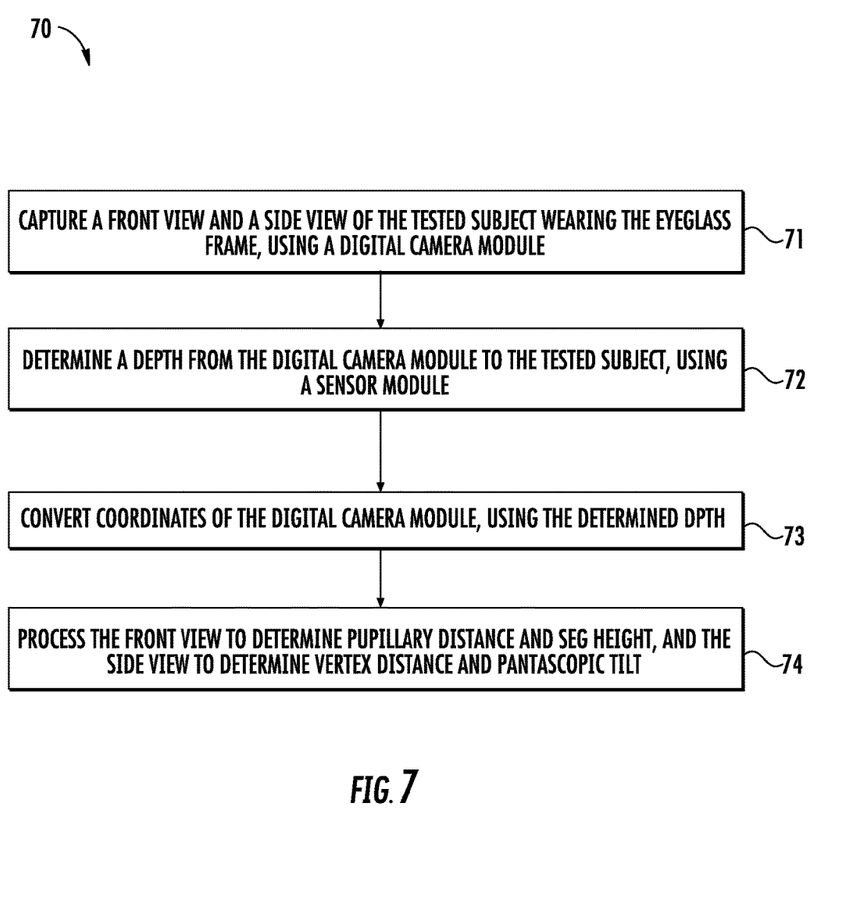
FIG. 7 shows a flow chart of another method for measuring human faces and eyeglass frames, in accordance with some embodiments.

In another embodiment of the present methods for measuring eyeglass frames worn by human subjects, a sensor module is used instead of a top view camera. As shown in the flow chart 70 of FIG. 7, the method begins with step 71 which involves capturing a plurality of digital images of a head of a tested subject wearing an eyeglass frame, using a digital camera module. The digital images include at least a front view and a side view of the face. In step 72, a sensor module is used to precisely determine a distance (depth in the z-direction in FIG. 5) from the digital camera module to the tested subject. In one embodiment, the sensor module can be a second camera that captures a side view. In another embodiment, the sensor module can be a 3D camera that captures two front view images of the tested subject. Using the binocular view of the face or the eyeglass frame captured by the 3D camera, the depth information of the tested subject to the eyeglass frame on the face is determined. In yet another embodiment, the sensor module can include an active source and a distance sensor for sensing the depth information of the tested subject or the eyeglass frame. For example, the active source may be a light source that sends a light beam to the head, and the distance sensor is a sensor that detects the reflected light off the head, from which the depth information is determined. A specific example of an active source/distance sensor is a laser distance sensor system. In more general examples, various types of proximity sensors may be utilized. In step 73, the determined depth (i.e., distance) from the digital camera module to the tested subject is used to convert coordinates of the digital camera module in pixels to physical measurements, such as millimeters, at the plane of the eyeglass frame. In step 74, a computer module is used to process the front view image for determining pupillary distances and seg heights, and to process the side view image for determining vertex distance and pantoscopic tilt. In some embodiments, the computer module may also store the images and the determined data.

While the specification has been described in detail with respect to specific embodiments of the invention, it will be appreciated that those skilled in the art, upon attaining an understanding of the foregoing, may readily conceive of alterations to, variations of, and equivalents to these embodiments. These and other modifications and variations to the present invention may be practiced by those skilled in the art, without departing from the scope of the present invention, which is more particularly set forth in the appended claims. Furthermore, those skilled in the art will appreciate that the foregoing description is by way of example only, and is not intended to limit the invention.

What is claimed is:

1. A method for making measurements for eyeglass frames worn by human subjects, the method comprising:
    capturing, using a first digital camera module, a plurality of images of a head of a tested subject wearing an eyeglass frame, wherein the plurality of images includes a front view image and a side view image of the head;
    monitoring, using a second camera module, a top view of the head;
    processing, using a computer module, the front view image and the side view image, wherein the front view image is used to determine a pupillary distance and a segment height, and the side view image is used to determine a vertex distance and a pantoscopic tilt, and wherein the computer module is connected to the second camera module; and
    determining, using the computer module and the top view of the head, an orientation of a plane of the eyeglass frame with respect to an optical axis of the first digital camera module, wherein the optical axis is a center line of the first digital camera module.

2. The method of claim 1, further comprising determining a calibration factor for the first digital camera module, the determining of the calibration factor comprising:
  using the top view of the head from the second camera module to determine a distance from the first digital camera module to the eyeglass frame or to a facial feature of the tested subject; and
  calculating the calibration factor using the determined distance;
  wherein the determining of the calibration factor is processed by the computer module.

3. The method of claim 2 wherein the calibration factor is in millimeters per pixel.

4. The method of claim 1:
  wherein the first digital camera module is coupled to a motion control module; and
  further comprising using the motion control module to move the first digital camera module to align an orientation of the front view image or the side view image with the optical axis of the first digital camera module, based on the top view of the head monitored by the second camera module.

5. The method of claim 4 wherein the motion control module moves the first digital camera module without any assistance of the tested subject.

6. The method of claim 4 wherein:
  the optical axis of the first digital camera module is aligned by the motion control module to be perpendicular to the plane of the eyeglass frame; and
  the computer module controls the motion control module using the top view from the second camera module.

7. The method of claim 4 wherein the motion control module comprises a rotation arm, and the moving of the first digital camera module comprises rotating the first digital camera module around the head of the tested subject.

8. The method of claim 1 wherein the first digital camera module and the second camera module are mounted to a motion control module, the motion control module comprising a mechanical structure, wherein:
  the first digital camera module is mounted on a first axis of the mechanical structure, and
  the second camera module is mounted on a second axis of the mechanical structure, the second axis being orthogonal to the first axis.

9. A system for making measurements for eyeglass frames worn by human subjects, comprising:
  a first digital camera module positioned to capture a plurality of images of a head of a tested subject wearing an eyeglass frame, wherein the plurality of images comprises a front view image and a side view image of the head;
  a second camera module positioned to monitor a top view of the head; and
  a computer module that processes the front view image to determine a pupillary distance and a segment height, the side view image to determine a vertex distance and a pantoscopic tilt and the top view to determine an orientation of a plane of the eyeglass frame with respect to an optical axis of the first digital camera module, wherein the optical axis is a center line of the first digital camera module.

10. The system of claim 9 wherein the computer module determines, using the top view of the head from the second camera module, a distance from the first digital camera module to the eyeglass frame or to a facial feature of the tested subject.

11. The system of claim 10, wherein the computer module determines a calibration factor in mm/pixel for the plurality of images of the first digital camera module, using the determined distance from the first digital camera module to the eyeglass frame.

12. The system of claim 9 further comprising a motion control module to which the first digital camera module is coupled, which moves the first digital camera module around the head to correct alignment of the front view image or the side view image;
  wherein the moving of the first digital camera module is monitored using the top view of the head from the second camera module.

13. The system of claim 12 wherein the motion control module comprises a rotation arm; and
  wherein the computer module controls the motion control module to move the rotation arm such that the optical axis of the first digital camera module is perpendicular to the plane of the eyeglass frame;
  wherein the computer module controls the motion control module using the top view from the second camera module.

14. The system of claim 12 wherein the motion control module comprises a rotation arm to which the first digital camera module and the second camera module are coupled, wherein an image coordinate axis for the second camera module rotates together with the rotation arm.

* * * * *